United States Patent [19]
Kaplan

[11] Patent Number: 6,048,517
[45] Date of Patent: Apr. 11, 2000

[54] HIGH SPF SUNSCREEN FORMULATIONS

[75] Inventor: Carl Kaplan, Memphis, Tenn.

[73] Assignee: Schering-Plough HealthCare Products, Inc., Memphis, Tenn.

[21] Appl. No.: 08/755,992

[22] Filed: Nov. 25, 1996

[51] Int. Cl.⁷ ..................................................... A61K 7/44
[52] U.S. Cl. ............................................... 424/60; 424/59
[58] Field of Search ........................................ 424/59, 60

[56] References Cited

U.S. PATENT DOCUMENTS

| | | | |
|---|---|---|---|
| 3,821,363 | 6/1974 | Black et al. | 424/59 |
| 4,387,089 | 6/1983 | De Polo | 424/59 |
| 4,522,807 | 6/1985 | Kaplan | 424/59 |
| 4,810,489 | 3/1989 | Murray et al. | 424/59 |
| 4,822,600 | 4/1989 | Wortzman | 424/59 |
| 4,917,882 | 4/1990 | Strobridge | 424/59 |
| 4,940,574 | 7/1990 | Kaplan | 424/59 |
| 5,204,090 | 4/1993 | Han | 424/59 |
| 5,208,011 | 5/1993 | Vaughan | 424/59 |
| 5,209,923 | 5/1993 | Nichols | 424/59 |
| 5,306,485 | 4/1994 | Robinson et al. | 424/59 |
| 5,306,486 | 4/1994 | McCook et al. | 424/59 |
| 5,445,815 | 8/1995 | Siegfried | 424/59 |
| 5,447,715 | 9/1995 | Roberts | 424/59 |
| 5,455,048 | 10/1995 | Lahmani et al. | 424/490 |
| 5,498,406 | 3/1996 | Nearn et al. | 424/59 |
| 5,543,136 | 8/1996 | Aldovs | 424/59 |
| 5,747,011 | 5/1998 | Ross et al. | 424/59 |
| 5,770,183 | 6/1998 | Linares | 424/59 |
| 5,783,174 | 7/1998 | Deckner | 424/59 |
| 5,876,699 | 3/1999 | DiSomma et al. | 424/59 |
| 5,980,871 | 11/1999 | Lukenbach et al. | 424/59 |
| 5,989,528 | 11/1999 | Tanner et al. | 424/59 |

FOREIGN PATENT DOCUMENTS

| | | | |
|---|---|---|---|
| 0 685 222 | 12/1995 | WIPO | A61K 7/42 |
| WO 97/25970 | 7/1997 | WIPO | A61K 7/42 |
| WO 97/49380 | 12/1997 | WIPO | A61K 7/40 |

OTHER PUBLICATIONS

Azizi et al. The Reliability of Sun Protection Factor. Photobiol. Sci. Its Appl., [Proc. Int. Congr. Photobiol.] 10th. pp. 897–9. (1991). Citation Only.

Greenoak.G. A Walk Across the SPF 15+ Ceiling: A Hole in the Floor is Sometimes Also a Hole in a Ceiling. Cosmetics Aerosols & Toiletries In Australia. 7(3): pp. 15–17, 21+. (Jan. 3, 1993). Citation Only.

T. Meadows, "The Effect of Various Sunscreen Combinations on a Product's SPF Value," *Journal of the Society of Cosmetic Chemists*, vol. 41, pp. 141–146, 1990.

J. C. Wang et al., "Effects of Waterproofness on the Clinical Efficacy and Irritation Potential of Sunscreen Products," *Cosmet. Pharm. Appl. Polym.,* [*Proc. Am. Chem. Soc. Symp. Polym. Cosmet. Pharm. Appl.*] 1990 (Publ. 1991), pp. 73–82.

S. Whitmore et al., "Prevention of UVB–Induced Immunosuppression in Humans by High Sun Protection Factor Sunscreens," *Archives of Dermatology*, vol. 131, pp. 1128–1133, 1995.

Kirk–Othmer, Encyclopedia of Chemical Technology, 4th Editioin, vol. 7, pp. 598–600, 1993.

*Primary Examiner*—Robert H. Harrison
*Attorney, Agent, or Firm*—Robert A. Franks

[57] ABSTRACT

Low cost sunscreening formulations having SPF values greater than 40 contain homosalate, octyl salicylate or mixtures thereof, in combination with oxybenzone, and optionally further contain octyl methoxycinnamate, avobenzone or mixtures thereof.

20 Claims, No Drawings

HIGH SPF SUNSCREEN FORMULATIONS

INTRODUCTION TO THE INVENTION

The present invention relates to compositions which absorb ultraviolet radiation, and more particularly to compositions which are applied to skin for protection against the effects of such radiation.

In this time of increased awareness of the health dangers from excessive exposure to ultraviolet radiation, the use of chemical and physical sunscreen formulations has become quite prevalent. Typical formulations are lotions, creams, ointments and gels which vary considerably in their ability to protect skin to which they are applied from the physical and biochemical effects of ultraviolet rays.

Sunscreens have evolved considerably over the years. Earlier formulations were intended to protect the user from sunburn during limited solar exposure, while transmitting sufficient ultraviolet irradiation to permit tanning of the skin. The focus today, however, is toward eliminating as much ultraviolet exposure as possible; this is primarily due to recent discoveries that any amount of unprotected exposure can potentially cause immune system suppression and lead to future health problems, such as skin carcinomas and other dermatological conditions. Tanning, rather than being aesthetically pleasing, is currently viewed by the medical community as a symptom of skin damage from overexposure to ultraviolet radiation.

The SPF (Sun Protection Factor) rating system has been developed to provide consumer guidance in selecting sunscreens. In general, the SPF number approximately corresponds to the multiple of time during which the sunscreen will prevent obvious reddening of the skin, over the exposure time that causes unprotected skin to exhibit reddening. Thus, a person should be able to remain in the sun without visible effects for eight times the usual unprotected duration, if an SPF 8 sunscreen formulation has been properly applied. The exposure needed to produce a visible effect varies from individual to individual, due to differences in their skin cells.

Active sunscreening agents in use during the "tanning" era have not been found useful for preparing the currently popular high-SPF "sunblock" products, which generally have SPF values above 40. The United States Food and Drug Administration published a Tentative Final Monograph ("TFM") listing approved sunscreen active ingredients, and acceptable concentrations of each in a formulation, in the *Federal Register* issue of Aug. 25, 1978. At this time, the SPF rating was not in general use in the United States. The TFM reported use of SPF values in Europe, and described SPF 3 formulations as providing minimal protection and being suitable for nonsensitive skin or skin already accustomed to the sun, SPF 4 as providing moderate protection and being suitable for normally sensitive skin, and SPF 6 as providing extra protection for sensitive skin.

Among the acceptable sunscreening agents in the TFM are homosalate (also called "homomenthyl salicylate") at 4 to 15 percent, octyl salicylate (also called "2-ethylhexyl salicylate") at 3 to 5 percent, octyl methoxycinnamate (also called "ethylhexyl p-methoxycinnamate") at 2 to 7.5 percent, and oxybenzone (also called "2-hydroxy-4-methoxybenzophenone" or "benzophenone-3") at 2 to 6 percent. The combination of 6 percent oxybenzone and 12 percent homosalate in an unspecified formulation was reported as having been used for skin and eye irritation testing, but no SPF or other sunscreening properties of the formulation were reported; the present inventor has determined an SPF value of about 38.5 for this combination, using the general formulation parameters of his examples, supra.

Also listed in the TFM is octocrylene (2-ethylhexyl 2-cyano-3,3-diphenylacrylate), a rather expensive compound having a large ultraviolet absorbing effectiveness, which is present in a majority of current high SPF commercially available sunblock formulations.

With the use of octocrylene to achieve high SPF has come a considerably higher cost of goods than was experienced when the older active ingredients were used for lower SPF products. Thus, it would be desirable to be able to formulate a high SPF sunblock formulation, using predominately (or only) the older, weaker low cost sunscreening agents.

Various combinations including homosalate, oxybenzone and octyl salicylate with octyl methoxycinnamate were reported by Meadows, "The Effect of Various Sunscreen Combinations on a Product's SPF Value," *Journal of the Society of Cosmetic Chemists*, Vol. 41, pages 141–146 (1990). U.S. Pat. No. 5,208,011 to Vaughan discloses sunscreen formulations containing octyl methoxycinnamate, octyl salicylate and oxybenzone. Whitmore et al., "Prevention of UVB-Induced Immunosuppression in Humans by a High Sun Protection Factor Sunscreen," *Archives of Dermatology*, Vol. 131, page 1129 (1995) reports the existence of a commercial sunscreen product having SPF 29 and containing octyl methoxycinnamate, oxybenzone and octyl salicylate. However, none of these predicts that high-SPF sunblockers can be prepared.

SUMMARY OF THE INVENTION

The present invention includes sunblocking compositions for application to the skin, having SPF values higher than 40 and containing active sunscreening ingredients selected from the group consisting of homosalate, octyl salicylate and mixtures thereof, in combination with oxybenzone and optionally also containing octyl methoxycinnamate or avobenzone, or both.

Such combinations provide unexpectedly high SPF values with relatively low-cost ingredients.

DETAILED DESCRIPTION OF THE INVENTION

In this application, the term "percent" shall mean percent by weight, unless the context clearly indicates otherwise. Many of the formulation components are identified herein by their names as given in the monographs of J. A. Wenninger et al., *CTFA Cosmetic Ingredient Handbook, Second Edition*, The Cosmetic, Toiletry and Fragrance Association, Inc., Washington, D.C., 1992. SPF values shall mean those values obtained with methods based upon the test procedures proposed to be Title 21 of the United States Code of Federal Regulations, Sections 352.70 through 352.77, which are tentatively in effect as provided in the *Federal Register*, Volume 58, Number 90 at pages 28298–28301 (May 12, 1993).

In accordance with the present invention, there are provided relatively low-cost sunblocking compositions having SPF values at least 40 and containing active sunscreening ingredients selected from the group consisting of about 4 to 15 percent homosalate, about 3 to 5 percent octyl salicylate and mixtures of any two or more thereof, in combination with about 2 to 6 percent oxybenzone. The compositions may also contain about 2 to 7.5 percent octyl methoxycinnamate, or about 2 to about 3 percent avobenzone, or both. Preferably, the SPF values will be at least about 45.

Homosalate, octyl salicylate and octyl methoxycinnamate are relatively low cost absorbers of solar radiation in the "UVB" region, considered to be about 290 to 320 nanometers in wavelength. Avobenzone is a relatively high cost absorber of solar radiation, but has the advantage of absorbing in the "UVA" region, about 320 to 400 nanometers. Since it is an important advantage of the invention that the sunscreen ingredients are low cost, the much more costly avobenzone will be included only where it is desired to add UVA absorbing protection to the typical sunscreen formulation.

Exemplary preferred formulations having SPF values greater than about 50 contain the following amounts of sunscreening active agents: (i) about 8 percent homosalate, about 7.5 percent octyl methoxycinnamate and about 6 percent oxybenzone, optionally also containing about 5 percent octyl salicylate; (ii) about 15 percent homosalate and about 6 percent oxybenzone, optionally also containing about 5 percent octyl salicylate; or (iii) about 8 percent homosalate, about 7.5 percent octyl methoxycinnamate, about 5 percent octyl salicylate, about 3 percent oxybenzone and about 3 percent avobenzone.

The invention resides in a discovery by the inventor that SPF values of such mixtures are much higher than would be predicted by simply adding the SPF values of the salicylates and the optionally present methoxycinnamate or avobenzone, or both, to that of the oxybenzone. While the scientific principles underlying this result presently have not been identified or fully explained by the inventor, the result appears to exist at all active ingredient concentrations relevant to the high SPF sunblock products of the invention and, surprisingly, becomes more pronounced at the higher concentrations.

In addition to the sunscreening active ingredients, the formulations contemplated by the inventor are typically emulsions such as lotions and creams, and therefore will contain several other components selected by the formulator from water, emulsifiers, emollients, fragrances, preservatives, vitamins, humectants, skin conditioners, antioxidants, waterproofing agents and others. The selection of appropriate ingredients and the mechanics of formulating emulsion products for skin contact are very well known to those skilled in the art.

The invention will be more fully explained by means of the following examples, which are not intended to limit the scope of the invention, as defined by the appended claims, in any manner.

EXAMPLE 1

Sunscreen formulations I–V are prepared, using the ingredient percentages shown in the following table. The formulation procedure involves: dissolving or dispersing water-soluble or -dispersable components in water to form an aqueous phase, and heating to about 80° C.; mixing the water-insoluble components together to form an oily phase, and heating to about 80° C.; then adding the oily mixture to the vigorously agitated aqueous mixture to form an emulsion. Mixing is then continued as the emulsion product cools to ambient temperature.

| COMPONENT | I | II | III | IV | V |
| --- | --- | --- | --- | --- | --- |
| Water | 69.24 | 56.265 | 58.265 | 53.24 | 50.265 |
| Oxybenzone | — | — | 6.00 | 6.00 | 6.00 |
| Sorbitan isostearate | — | 4.00 | 4.00 | — | 4.00 |
| Sorbitol, 70% aqueous solution | 5.00 | 5.00 | 5.00 | 5.00 | 5.00 |
| Sorbitan oleate | 4.00 | — | — | 4.00 | — |
| Polyglyceryl-3 distearate | — | 3.00 | 3.00 | — | 3.00 |
| Octyl salicylate | 3.00 | 5.00 | — | — | 5.00 |
| Glyceryl stearate, self emulsifying | 3.00 | — | — | 3.00 | — |
| Sorbitan stearate | 3.00 | — | — | 3.00 | — |
| Vegetable oil | 2.00 | — | — | 2.00 | — |
| Homosalate | 2.00 | 15.00 | 12.00 | 15.00 | 15.00 |
| Stearic acid | 2.00 | 2.00 | 2.00 | 2.00 | 2.00 |
| Octadecene/maleic anhydride copolymer | 2.00 | 3.00 | 3.00 | 2.00 | 3.00 |
| Triethanolamine | 1.80 | 2.25 | 2.25 | 1.80 | 2.25 |
| Barium sulfate | — | 1.75 | 1.75 | — | 1.75 |
| Benzyl alcohol | 1.00 | 1.00 | 1.00 | 1.00 | 1.00 |
| Fragrance | 0.60 | 0.60 | 0.60 | 0.60 | 0.60 |
| Dimethicone | 0.40 | 0.40 | 0.40 | 0.40 | 0.40 |
| Magnesium aluminum silicate | 0.25 | — | — | 0.25 | — |
| Imidazolidinyl urea | 0.20 | 0.20 | 0.20 | 0.20 | 0.20 |
| Methylparaben | 0.20 | 0.20 | 0.20 | 0.20 | 0.20 |
| Propylparaben | 0.10 | 0.10 | 0.10 | 0.10 | 0.10 |
| Vitamin E | 0.10 | 0.10 | 0.10 | 0.10 | 0.10 |
| Jojoba oil | 0.05 | 0.05 | 0.05 | 0.05 | 0.05 |
| Aloe vera lipoquinone | 0.05 | 0.05 | 0.05 | 0.05 | 0.05 |
| Carbomer | — | 0.025 | 0.025 | — | 0.025 |
| Disodium EDTA | 0.01 | 0.01 | 0.01 | 0.01 | 0.01 |
| SPF value | 4.5 | 9.8 | 38.5 | 49.1 | 51.8 |

SPF data from the table above can be plotted on a graph wherein the y-axis is calibrated in SPF values and the x-axis shows total salicylate sunscreen ingredient concentration, in percent. A broken line may be placed thereon for a formulation actually containing no salicylates, but having only 6 percent oxybenzone as the active sunscreen ingredient; the SPF value for this formulation is 8.47 and a broken line is extended from the data point solely to facilitate comparisons.

A line is generated from SPF testing of formulations "I" and "II" in the table above. The equation of this line is:

$$SPF=0.42(\text{Percent Salicylates})+1.60$$

and adding the SPF 8.47 value for the oxybenzone formulation (while also subtracting the SPF of 1 commonly found for "placebo" formulations) gives an equation for a line as:

$$SPF=0.42(\text{Percent Salicylates})+9.07$$

which may also be drawn as a broken line.

When SPF data for formulations "III," "IV" and "V" above are plotted, another line is obtained, having the equation:

$$SPF=2.22(\text{Percent Salicylates})+11.44$$

which indicates that these data do not follow the prediction of the above-mentioned broken line, but indicate SPF values which are unexpectedly high.

EXAMPLE 2

A UVA/UVB sunscreen lotion having an SPF value greater than 50 is prepared from the following components:

| Ingredient | * | Percent |
| --- | --- | --- |
| Water | | 50.965 |
| Homomenthyl salicylate | A | 8.00 |
| Octyl methoxycinnamate | A | 7.50 |
| Sorbitol, 70% aqueous solution | E | 5.00 |
| Octyl salicylate | | 5.00 |
| Sorbitan isostearate | A | 4.00 |
| Oxybenzone | A | 3.00 |
| Polyglyceryl-3 distearate | A | 3.00 |
| Octadecene/maleic anhydride copolymer | B | 3.00 |
| Triethanolamine | E | 2.25 |
| Stearic acid | A | 2.00 |
| Avobenzone | A | 2.00 |
| Barium sulfate | C | 1.75 |
| Benzyl alcohol | G | 1.00 |
| Fragrance | G | 0.60 |
| Dimethicone | B | 0.40 |
| Methylparaben | E | 0.20 |
| Propylparaben | A | 0.10 |
| Vitamin E | A | 0.10 |
| Aloe vera lipoquinone | A | 0.05 |
| Jojoba oil | A | 0.05 |
| Carbomer | D | 0.025 |
| Disodium EDTA | E | 0.01 |

*Indicates addition in a particular formulation procedure step.

The lotion is prepared as follows: (1) all of the "A" components and about one-third of the octyl salicylate are mixed and heated to about 76–82° C., to form a solution; (2) the "B" components are sequentially added to the step 1 solution, with continued mixing; (3) the "C" component is sprinkled into the remaining octyl salicylate and vigorously mixed, then that mixture is added to the step 2 mixture; (4) about half of the water is mixed with the "D" component to form a uniform dispersion, then the remaining water and the "E" components are added and heated to about 76–82° C., with mixing; (5) the hot mixture from step 3 is added to the hot dispersion from step 4, with mixing to form an emulsion, and the emulsion is allowed to cool to room temperature with continued mixing; (6) as the temperature of the emulsion passes through about 49° C., the "G" components are added; and (7) after cooling, water is added to the emulsion to compensate for evaporative losses during the preparation.

EXAMPLE 3

Using the general procedure of the preceding example, a sunscreen lotion having an SPF value greater than 50 is prepared from the following components:

| Ingredient | * | Percent |
| --- | --- | --- |
| Water | | 49.765 |
| Homomenthyl salicylate | A | 8.00 |
| Octyl methoxycinnamate | A | 7.50 |
| Oxybenzone | A | 6.00 |
| Sorbitol, 70% aqueous solution | E | 5.00 |
| Octyl salicylate | | 5.00 |
| Sorbitan isostearate | A | 4.00 |
| Polyglyceryl-3 distearate | A | 3.00 |
| Octadecene/maleic anhydride copolymer | B | 3.00 |
| Triethanolamine | E | 2.25 |
| Stearic acid | A | 2.00 |
| Barium sulfate | C | 1.75 |
| Benzyl alcohol | G | 1.00 |
| Fragrance | G | 0.60 |
| Dimethicone | B | 0.40 |
| Methylparaben | E | 0.20 |
| Imidazolidinyl urea | F | 0.20 |
| Propylparaben | A | 0.10 |
| Vitamin E | B | 0.10 |
| Aloe vera lipoquinone | A | 0.05 |
| Jojoba oil | A | 0.05 |
| Carbomer | D | 0.025 |
| Disodium EDTA | E | 0.01 |

EXAMPLE 4

Using the general procedure of Example 2, a sunscreen lotion having an SPF value greater than 50 is prepared from the following components:

| Ingredient | * | Percent |
| --- | --- | --- |
| Water | | 54.765 |
| Homomenthyl salicylate | | 8.00 |
| Octyl methoxycinnamate | A | 7.50 |
| Oxybenzone | A | 6.00 |
| Sorbitol, 70% aqueous solution | E | 5.00 |
| Sorbitan isostearate | A | 4.00 |
| Polyglyceryl-3 distearate | A | 3.00 |
| Octadecene/maleic anhydride copolymer | B | 3.00 |
| Triethanolamine | E | 2.25 |
| Stearic acid | A | 2.00 |
| Barium sulfate | C | 1.75 |
| Benzyl alcohol | G | 1.00 |
| Fragrance | G | 0.60 |
| Dimethicone | B | 0.40 |
| Methylparaben | E | 0.20 |
| Imidazolidinyl urea | F | 0.20 |
| Propylparaben | A | 0.10 |
| Vitamin E | B | 0.10 |
| Aloe vera lipoquinone | A | 0.05 |
| Jojoba oil | A | 0.05 |
| Carbomer | D | 0.025 |
| Disodium EDTA | E | 0.01 |

In this preparation, about half of the homomenthyl salicylate is added as an "A" component, while the remaining portion is mixed with the barium sulfate before its addition.

What is claimed is:

1. A sunscreening composition having SPF values at least 40, wherein the sunscreening ingredients consist of: (a) homosalate and oxybenzone, combined in amounts sufficient to obtain SPF values at least 40; or (b) homosalate and oxybenzone, combined in amounts sufficient to obtain SPF values at least 40, in further combination with octyl salicylate, octyl methoxycinnamate, avobenzone or mixtures of any two or more thereof.

2. The composition of claim 1, having SPF values about 45 or greater.

3. The composition of claim 1, having SPF values about 50 or greater.

4. The composition of claim 1, wherein homosalate is present at 4 to 15 percent by weight.

5. The composition of claim 1, wherein octyl salicylate is present at 3 to 5 percent by weight.

6. The composition of claim 1, wherein oxybenzone is present at 2 to 6 percent by weight.

7. The composition of claim 1, wherein octyl methoxycinnamate is present at 2 to 7.5 percent by weight.

8. The composition of claim 1, wherein avobenzone is present at 2 to 3 percent by weight.

9. The composition of claim 1, wherein homosalate and octyl salicylate are present in total concentrations at least about 13 percent by weight.

10. The composition of claim 1, wherein oxybenzone is present in concentrations at least about 3 percent by weight.

11. The composition of claim 1, wherein homosalate is present at about 15 percent by weight and oxybenzone is present at about 6 percent by weight.

12. The composition of claim 11, further containing about 5 weight percent octyl salicylate.

13. The composition of claim 1, wherein homosalate is present at about 8 percent by weight, octyl methoxycinnamate is present at about 7.5 percent by weight and oxybenzone is present at about 6 percent by weight.

14. The composition of claim 13, further containing about 5 weight percent octyl salicylate.

15. A sunscreening composition having SPF values at least 40, wherein the sunscreening ingredients consist of: (a) 4 to 15 weight percent homosalate, alone or in admixture with 3 to 5 weight percent octyl salicylate, in combination with 2 to 6 weight percent oxybenzone, the combination being sufficient to obtain SPF values at least 40; or (b) 4 to 15 weight percent homosalate, alone or in admixture with 3 to 5 weight percent octyl salicylate, in combination with 2 to 6 weight percent oxybenzone, the combination being sufficient to obtain SPF values at least 40, in further combination with 2 to 7.5 weight percent octyl methoxycinnamate, 2 to 3 weight percent avobenzone or mixtures thereof.

16. The composition of claim 15, wherein homosalate is present at about 15 percent by weight and oxybenzone is present at about 6 percent by weight.

17. The composition of claim 16, further containing about 5 weight percent octyl salicylate.

18. The composition of claim 15, wherein homosalate is present at about 8 percent by weight, octyl methoxycinnamate is present at about 7.5 percent by weight and oxybenzone is present at about 6 percent by weight.

19. The composition of claim 18, further containing about 5 weight percent octyl salicylate.

20. A sunscreening composition having SPF values at least 40, wherein the sunscreening ingredients are about 8 to about 15 weight percent homosalate, about 6 weight percent oxybenzone, up to about 5 weight percent octyl salicylate, up to about 3 weight percent avobenzone and up to about 7.5 weight percent octyl methoxycinnamate, the amounts of homosalate, octyl salicylate and oxybenzone together being sufficient to obtain SPF values at least 40.

* * * * *